United States Patent [19]

Nozaki

[11] 4,229,606

[45] Oct. 21, 1980

[54] 1,7-OCTADIENE PROCESS

[75] Inventor: Kenzie Nozaki, Houston, Tex.

[73] Assignee: Shell Oil Company, Houston, Tex.

[21] Appl. No.: 968,883

[22] Filed: Dec. 13, 1978

[51] Int. Cl.$^2$ ............................................. C07C 11/12
[52] U.S. Cl. .................................... 585/509; 585/503; 585/506; 585/627; 252/431 P; 260/429 R
[58] Field of Search ............... 585/509, 627, 503, 506; 252/431 P

[56] References Cited

U.S. PATENT DOCUMENTS

| | | | |
|---|---|---|---|
| 3,732,328 | 5/1973 | Wright | 260/680 B |
| 3,823,199 | 7/1974 | Wright | 260/680 B |
| 3,992,456 | 11/1976 | Atkins et al. | 568/903 |
| 4,100,194 | 6/1978 | Hobbs et al. | 252/431 P |

FOREIGN PATENT DOCUMENTS 1341324 12/1973 United Kingdom .

OTHER PUBLICATIONS

Roffia et al., J. Orgmet Chem. 55 (1973) pp. 405–407.
Gardner et al., Tet. Letters, 1972, #2, pp. 163–164.
Couch et al., J. Chem. Soc. (Dalton) 1974, #12, pp. 1309–1313.
Pittman et al., Chem. Abst. 86 (1977) #54628.

*Primary Examiner*—Arthur P. Demers
*Attorney, Agent, or Firm*—Howard W. Haworth

[57] ABSTRACT

A process for preparing 1,7-octadiene by hydrodimerizing butadiene which comprises reacting the butadiene in the presence of formic acid, or a salt thereof, optionally a solvent and a catalyst comprising palladium complexed with a sterically hindered phosphine, phosphinite or phosphonite and a different ligand selected from phosphine, phosphinite, phosphonite or phosphite. Enhanced catalytic activity is obtained.

8 Claims, No Drawings

1,7-OCTADIENE PROCESS

BACKGROUND OF THE INVENTION

1. Field of the Invention

The present invention relates to the production of 1,7-octadiene by hydrodimerizing butadiene.

2. Description of the Prior Art

Hydrodimerizing butadiene with formic acid and palladium catalyst is known. Wright in U.S. Pat. No. 3,732,328 issued May 8, 1973, prepares mixtures of octadienes by reacting butadiene in the presence of a palladium compound, a polar solvent, a reducing agent and a tertiary phosphine. Wright in U.S. Pat. No. 3,832,199, issued July 9, 1974, prepares mixtures of octadiene by reacting butadienes in the presence of a palladium compound, a non-polar solvent, a reducing agent and a tertiary phosphine. Wright in British Pat. No. 1,341,324 issued Dec. 9, 1973 discloses processes similar to above. Gardner et al, Tetrahedron Letters No. 2, pp. 163–164 discloses the production of mixtures of octadiene by reacting butadiene in the presence of palladium salts, or organic base, formic acid and a phosphine. Roffia et al, Journal of Organometallic Chemistry, 55 (1973) 405–507 utilizes a phosphine-zero valent palladium complex catalyst in benzene in the presence of formic acid to dimerize butadiene.

The prior art has not recognized the advantages of utilizing mixtures of different tertiary organo phosphine compounds to enhance catalyst activity.

SUMMARY OF THE INVENTION

The process of this invention is directed to the hydrodimerization of butadiene to 1,7-octadiene by reacting butadiene in the presence of formic acid or a salt of formic acid, optionally a solvent, and a catalyst comprising palladium complexed with selected mixtures of tertiary organophosphorus ligands. The mixture of ligands utilized comprises one ligand selected from the group consisting of tertiary organophosphines, phosphinites and phosphonites represented by the formula $(RO)_a PR_b$ where $a+b$ equals 3, a is 0, 1 or 2, and at least one R is benzyl or branched alkyl, aralkyl, alkenyl or cycloalkyl having from 3 to about 10 carbon atoms with branching occurring at a carbon atom no more than two carbon atoms from the phosphorus atoms, and at least one other ligand selected from the group consisting of tertiary organo phosphines, phosphinites, phosphonites and phosphites represented by the formula $(RO)_{a'} PR_{b'}$, where $a'+b'$ equals 3, a' is 0, 1, 2 or 3, and a' is not the same as a. Thus, one of the ligands is a sterically hindered phosphine, phosphinite or phosphonite and the other ligand is phosphine, phosphinite, phosphonite or phosphite which may or may not be sterically hindered, preferably not sterically hindered and is preferably selected from a different class. This selection of ligands provides a synergistic improvement in catalytic activity.

DESCRIPTION OF THE PREFERRED EMBODIMENTS

Solvents are not essential to the process of this invention, but a good organic solvent can promote the rate of reaction by a factor of two or more.

Wright in above-cited U.S. Pat. No. 3,823,199 cites the use of non-polar solvents such as paraffinic, cycloparaffinic or aromatic which are also useful in the process of this invention. The solvent can be a paraffin or cycloparaffin containing 5 to 16 carbon atoms, and the like. Suitable solvents also include aromatic hydrocarbons such as benzene, lower alkyl substituted hydrocarbons such as toluene, m-, p- and o-xylene, halogenated aromatic hydrocarbons including chloro, bromo and iodo substituted, such as chlorobenzene and the like. Halogenated lower aliphatic compounds such as chloroform, methylene chloride, carbon tetrachloride and the like may be used, in particular chloroform is preferred.

Further useful are amine solvents such as those cited by Wright in above-noted British Pat. No. 1,341,324. A wide range of amines are useful provided that they are liquid under reaction conditions. Tertiary amines are preferred to primary and secondary amines. Suitable amine solvents include alkylamines, cycloalkylamines, arylamines and heterocyclic amines such as morpholine, pyridine, piperazine and piperidine. Examples of these classes of amines are the lower alkylamines containing 2 to 6 carbon atoms in each alkyl group such as triethylamine; mono-cyclohexylamine, and N-alkyl-cyclohexylamines containing up to 12 carbon atoms; aniline and N-alkylanilines containing up to 12 carbon atoms and N-alkylmorpholines containing up to 12 carbon atoms.

Solvents of moderate coordinating ability are quite useful and include nitriles such as lower alkyl nitriles, hydrocarbon aromatic nitriles including acetonitrile, benzonitrile and the like, amides including benzamide, acetamide, mono- and di-substituted amides where the substituent is preferably lower alkyl. Suitable substituted amides include N-methyl acetamide, N,N dimethyl acetamide and dimethylformamide. Dialkyl sulfoxides such as dimethyl sulfoxide and sulfones such as sulfolane and alkyl-substituted sulfolane are satisfactory. By dialkyl it is meant that the sulfur and nitrogen atoms are connected to two different carbon atoms. They may be separate alkyl groups or the same, i.e., a ring alkyl group, e.g., tetramethylene sulfoxide and N-methyl pyrrolidinone. The alkyl moieties have carbon numbers ranging from 1 to about 6. Simple ethers such as the dilower alkyl ethers including dimethyl ether, diethylene, and the like, function satisfactorily. Hydrocarbon aromatic ethers such as the lower alkyl phenyl ethers may be also used. In addition, the cyclic diethers such as 1,4-dioxane are also suitable solvents.

Simple lower alkyl esters of lower alkanoic acids such as ethyl acetate, methyl acetate, methyl butyrate and the like as well as cyclic diesters such as ethylene carbonate are also suitable solvents of moderate coordinating ability. Ketones, including lower aliphatic ketones such as methyl ethyl ketone and hydrocarbon aromatic ketones such as acetophenone are also satisfactory solvents. Lower mono- and di-alkanols such as isopropanol, ethylene glycol and the like may be used if desired. The preferred solvents of moderate coordinating ability include nitriles, formamides, such as dimethylformamide, dilower alkyl ethers, lower alkyl phenyl ethers, simple lower alkyl esters of lower alkanoic acids, ketones and lower alkanols.

The particularly preferred solvents utilized in this invention include benzene, dimethylformamide, chlorobenzene, anisol, N,N-dimethylacetamide, nitromethane, ethyl acetate, isopropanol, benzonitrile, chloroform, methyl ether ketone, acetonitrile, diethylether, acetophenoneon, toluene, ethylene glycol, ethyl carbonate, propylene carbonate and sulfolane. Particularly desired solvents are nitromethane, ethylene carbonate and propylene carbonate.

The preferred organic solvents will have carbon numbers ranging from 1 to about 20. Particularly desired solvents are those which give two-phase systems which allow easy product separation such as, for example, nitromethane, ethylene carbonate and propylene carbonate.

The amount of solvent added should be sufficient to dissolve the palladium compound-tertiary organo phosphorus complex.

The formic acid is utilized as a source of hydrogen for the process. It is present in the reaction mixture as an acid or as a salt of a base. When the salt is used, it is thought that dissociation of the formic acid-base salt provides a suitable amount of formic acid necessary to provide the required hydrogen.

It is desirable that some formic acid or the salt, be present during the entire course of the reaction. When operating the process batch-wise, this can be accomplished by adding a stoichiometric amount of formic acid initially, 1 mole of formic acid for every 2 moles of butadiene, or by continuously or periodically adding additional amounts of formic acid.

A base when used must be one which can neutralize formic acid according to the reaction:

$$HCOOH + B \rightarrow HCOO^- HB^+.$$

The base may be organic or inorganic. Suitable organic bases typically have dissociation constants greater than $10^{-8}$ and include tertiary amines such as triethyl amine, tributyl amine, dimethylethyl amine, lutidine, tripropyl amine, N-methyl morpholine, isoquinoline. N-methyl-2,2,6,6-tetramethyl piperidine, 2,8-(dimethylamine) naphthalene and the like.

Suitable inorganic bases include ammonia, the hydroxide bases such as sodium hydroxide, potassium hydroxide, calcium hydroxide; ammonium hydroxide; the carbonates and bicarbonates such as sodium carbonate, sodium bicarbonate, potassium carbonate, potassium bicarbonate, sodium bicarbonate, potassium carbonate, potassium bicarbonate, calcium carbonate and the like; the weak bases such as sodium acetate, potassium acetate, ammonium carbonate, ammonium acetate and the like. When the inorganic bases are utilized, small amounts of water may be present. Preferred moles of water are at least equal to the moles of formate salts.

When organic bases are utilized, excess base may be utilized as a solvent or the amine-base salt may be used as the solvent.

The catalyst used in the process of this invention is palladium or a palladium compound complexed with a trisorgano phosphorus-containing ligands. The palladium may be in any of its possible valence states, e.g. o, +2, etc. Suitable palladium compounds include the palladium carboxylates, particularly palladium carboxylates derived from alkanoic acids containing up to six carbon atoms such as palladium acetate (OAC), complexes such as palladium acetylacetonate (AcAc), bis-benzonitrile palladium (II) and lithium palladous chloride as well as the palladium halides, nitrates and sulfates such as palladous chloride and palladium nitrate $(Pd(NO_3)_2(OH)_2$ and palladium sulfate. The palladium is present in the reaction mixture in catalytic amounts; preferably from about 1 to about $10^{-6}$ molar and more preferably from about $10^{-1}$ to about $10^{-4}$ molar.

The palladium compounds complexed with a trisorgano phosphorus-containing ligand are typically prepared by reacting the tertiary phosphorus ligand with the appropriate palladium compound as, for example represented by the following equations:

$$(RO)_aPR_b + (RO)_{a'} + (PhCN)_2PdCl_2 \rightarrow [(RO)_aPR_b][(RO)_{a'}PR_{b'}]PdCl_2$$

$$[(RO)_aPR_b][(RO)_{a'}PR_{b'}]PdCl_2 + Ag_2Co_3 \rightarrow [(RO)_aPR_b][(RO)_{a'}PR_{b'}]PdCO_3$$

$$[(RO)_aPR_b][(RO)_{a'}PR_{b'}]PdSO_4 + SO_2 \rightarrow [(RO)_aPR_b][(RO)_{a'}PR_{b'}]PdSO_4$$

$$[(RO)_aPR_b][(RO)_{a'}PR_{b'}]PdO_2 + N_2O_4 \rightarrow [(RO)_aPr_b][(RO)_{a'}PR_{b'}]Pd(NO_3)_2$$

where $[(RO)_aPR_b][(RO)_{a'}PR_{b'}]$ represents the mixture of ligands of the present invention and R, a, b, a' and b' are defined below.

The ligands used in the present invention will comprise a mixture of two ligands which provide a synergistic improvement in catalytic activity over the use of the individual ligands. A first ligand present in the amount of at least one mole of ligand per mole of palladium is a sterically hindered tertiary organophosphorus compound selected from one of the following three classes of tertiary organo phosphorus compounds: phosphines, phosphinites and phosphonites; which can be represented by the following general formula:

$$(RO)_aPR_b$$

where a+b equals, 3, a is 0, 1 or 2 and R generally is hydrocarbyl and may be the same or different and is selected from aryl, alkyl, aralkyl and alkaryl groups which contain less than about 20 carbon atoms, preferably less than about 12 carbon atoms, with at least one of the R moieties being a sterically hindering moiety being selected from the group consisting of benzyl, or branched alkyl, aralkyl, alkenyl and cycloalkyl having from 3 to about 10 carbon atoms with branching occurring at a carbon atom no more than two carbon atoms from the phosphorus atom.

Suitable examples of R in general are phenyl, p-tolyl, o-tolyl, m-tolyl, m-chlorophenyl, p-anioly, m-anisoyl, ethyl, propyl, butyl and the like. It is also suitable for the organic radical R to contain functional groups or to satisfy more than one of the valences of the phosphorus atom, thereby forming a heterocyclic compound with the phosphorus atom. Preferably R represents aryl, alkyl, aralkyl, alkaryl or a mixture thereof having carbon numbers from 1 to about 20, preferably 1 to about 12 carbon atoms and need not be the same, e.g., $R^1R^2R^3P$, $(R^1O)PR^2R^3$, $(R^1O)(R^2O)PR^3$, $R^1PR^2$.

Illustrative of the sterically hindering R moiety are, for alkyl, isopropyl sec-butyl, tert-butyl, isobutyl, neopentyl, sec-pentyl, tert-pentyl, 2-methylbutyl, sec-hexyl, tert-hexyl, 2,2-dimethylpropyl; for aralkyl, alpha-methylbenzyl, alpha, alpha-dimethylbenzyl, alpha-methyl-alpha-ethylbenzyl, phenylethyl, phenylisopropyl, phenyl-tert-butyl; for alkenyl, allyl, crotyl, methallyl, 1-methylethenyl, 1-methyl-2-propenyl, 2-methyl-2-propenyl, 1,1-dimethyl-2-propenyl, 1-methyl-3-butenyl and, for cycloalkyl, cyclopropyl, cyclobutyl, cyclopentyl, cyclohexyl, cycloheptyl, and the like.

Alternatively the formula for the first ligand can be expressed as:

$$R_c{}^1R_d{}^2R_e{}^3P(OR^4)_f(OR^5)_g \quad \text{(II)}$$

where c, d, e, f and g individually equals 0 or 1, c+d+e+f+g equals 3 and R is as defined above. $R^1$, $R^2$, $R^3$, $R^4$ and $R^5$ may be the same or different. Again, it must be emphasized, that at least one of the R moieties must be a sterically hindering moiety and is selected from benzyl or branched alkyl, aralkyl, alkenyl, and cycloalkyl having from 3 to about 10 carbon atoms with branching occurring at a carbon atom no more than two carbon atoms from the phosphorus atom. This R moiety provides a steric hinderance to the catalyst complex which enhances selectivity.

A second ligand present in the amount of at least one mole of ligand per mole of palladium is a tertiary organo phosphorus compound of a different class than the first ligand and is selected from one of the following classes of tertiary organic phosphorus compounds: phosphines, phosphinites, phosphonites and phosphites. This second ligand can be represented by the following general formula:

$$(RO)_{a'}PR_{b'} \quad \text{(III)}$$

where a'+b' equals 3, a' is 0, 1, 2 or 3, a' is not the same as a above and R generally is hydrocarbyl and may be the same or different and is selected from aryl, alkyl, aralkyl and alkaryl groups which contain less than about 20 carbon atoms, preferably less than about 12 carbon atom.

Suitable examples of R are phenyl, p-tolyl, o-tolyl, m-tolyl, m-chlorophenyl, p-anisoly, m-anisoyl, ethyl, propyl, butyl and the like. It is also suitable for the organic radical R to contain functional groups or to satisfy more than one of the valences of the phosphorus atoms, thereby forming a heterocyclic compound with the phosphorus atom. Preferably R represents aryl, alkyl, aralkyl, alkaryl or a mixture thereof having carbon numbers from 1 to about 20, preferably 1 to about 12 carbon atoms and need not be the same, e.g. $R^1R^2R^3P$, $(R^1O)PR^2R^3$, $(R^1O)(R^1O)PR^3$, $R^1PR^2$.

Alternatively, the formula from the second ligand can be expressed as:

$$R_h{}^1R_i{}^2R_j{}^3P(OR^4)_k(OR^5)_l(OR^6) \quad \text{(IV)}$$

where h, i, j, k, l and m are individually 0 or 1, h+i+j+k+l+m equals 3 and R is as defined generally above. $R^1$, $R^2$, $R^3$, $R^4$, $R^5$ and $R^6$ may be the same or different. The second ligand may or may not have sterically hindering moieties incorporated therein.

The mole ratio of tertiary phosphorus ligand to palladium is at least 2. Preferably the mole ratio of ligand to palladium ranges from about 2:1 to about 20:1 and preferably from about 2:1 to about 5:1. The use of the tertiary phosphorus ligands of the invention provide extremely high selectivities to 1,7-octaidene as well as high activity for conversion of butadiene.

Alternatively, the palladium compound and the tertiary phosphorus ligand may be bound onto a crosslinked synthetic resin instead of being dissolved in the reaction medium. Acceptable crosslinked synthetic resins include crosslinked polystyrene, poly(alpha-alkyl) acrylates, polycarbonates, polyamides and the like. In general, one of the ligands will be bound to the resin and will have the generic formula:

$$Z-P(RO)_nR_p \quad \text{(V)}$$

wherein R is as generally defined above, n is an integer from 0 to 2, p is 2-n and Z is the crosslinked synthetic resin. When the bound ligand is as defined by equations (V) and (VI), is the first ligand having at least one sterically hindering moiety as defined above, then the second ligand is defined as above in equations (III) and (IV). When the unbound ligand is the first ligand as defined in equations (I) and (II) then the second ligand is the bound ligand as defined in equations (V) and (VI) but which may or may not have sterically hindering moieties.

The bound tertiary phosphine may have the general formula:

$$\begin{array}{c}(R_6)_q-(R_6)_r\\ |\\ (RO)_{\overline{n}}P-R_p\end{array} \quad \text{(VI)}$$

wherein R, n and p are defined previously, and $R_6$ represents the repeating unit of the synthetic resin and where q is a positive integer, r is 0 or a positive integer, q+r equals the total number of repeating units in resin and the percentage of the repeating units substituted with the tertiary phosphine is represented by the formula:

$$\frac{8q}{q+r} \times 100\%.$$

The number of repeating units substituted with the tertiary phosphine is not critical. When less than 5% of the repeating units contain a phosphine substitute, large quantities of the resin must be used to form the bound catalyst. Accordingly, it is desirable to have a least 10% of the repeating units substituted with a tertiary phosphine. It is preferred, however, that from 20 to 40% of the repeating units contain a phosphine substituent. The substituent can be introduced into the resin using well-known techniques, such as those described by Smith et al in the Journal of the American Chemical Society, 97 (7) 1749 (1975) and by Pittman et al in Ann. N.Y. Academy of Sciences, 239, 76 (1974). In accordance with those techniques, the palladium compound is complexed with the phosphorus-substituted resin by admixing in a solvent for the palladium compound.

The catalyst may be pretreated to enhance reactivity by contacting it with a reducing agent at a temperature of from about 20° to about 90° C. for from about 0.1 to about 5 hours. The reducing agent may be gaseous, solid or liquid. Examples of gaseous agents are hydrogen, and carbon monoxide. Examples of liquid or solid reducing agents are hydrazine, $NaBH_4$, $NaOCH_3$, (isopropyl)$_3$P, Cu, Na, and Al alkyls, etc. The reduction may be carried out in a separate autoclave or preferably is carried out in the hydrodimerization reactor prior to the introduction of the butadiene. The palladium compound-trisorganophosphorus complex may be dissolved in the solvent used in this invention prior to reduction.

The process can be either continuous or batch. The reaction temperature of the process is not critical, however, it is preferred to maintain the reaction between about 0° to about 100° C. preferably between about 20° to about 70° C. The process is conducted under a sufficient pressure to maintain liquid phase conditions at the reaction temperature. Typically the pressure is autogeneous.

The process of this invention is particularly useful when a BBB stream from an oil pyrolysis unit is utilized to provide the butadiene. These BBB streams are the C₄ cut from a thermal cracking unit typically containing 30-40% butadiene, 20-35% isobutene and 20-30% n-butenes and many minor components.

The process of this invention will be further described by the following illustrative embodiments which are provided for illustration and are not to be construed as limiting the invention.

ILLUSTRATIVE EMBODIMENTS

Illustrative Embodiment I

To an 80 milliliter glass-lined autoclave were charged $2.7 \times 10^{-5}$ moles of palladium as a 10% water solution of $Pd(NO_3)_2(OH)_2$, 10 ml of pyridine, 2 g of butadiene, $1.85 \times 10^{-2}$ moles of formic acid salt ($Et_3N \cdot HOOCH$) and sufficient phosphorus ligand to provide the appropriate ligand to palladium ratio as shown in Table 1 below. The stirred reactor was heated to 40° C. for two hours, cooled and the product was analyzed by gas chromatography and mass spectrography. The results are shown in the following table.

TABLE I

| Example | Phosphite | P/Pd Ratio | Phosphine | P/Pd Ratio | Butadiene Conversion mol % | 1,7-Octadiene Selectivity mol % |
|---|---|---|---|---|---|---|
| 1 | — | — | P(isopropyl)₃ | 1 | 21.0 | 95.5 |
| 2 | — | — | P(isopropyl)₃ | 2 | 30.0 | 98.0 |
| 3 | P(O CH₃)₃ | 1 | — | — | 8.5 | 71.0 |
| 4 | P(O CH₃)₃ | 2 | — | — | 10.0 | 72.0 |
| 5 | P(O Ethyl)₃ | 1 | — | — | 5.2 | 67.0 |
| 6 | P(O Ethyl)₃ | 2 | — | — | 11.0 | 78.0 |
| 7 | P(O isopropyl)₃ | 1 | — | — | 5.5 | 59.0 |
| 8 | P(O isopropyl)₃ | 2 | — | — | 16.0 | 76.0 |
| 9 | P(O n-butyl)₃ | 2 | — | — | 1.8 | 80.0 |
| 10 | P(O Phenyl)₃ | 1 | — | — | 1.7 | 75.0 |
| 11 | P(O Phenyl)₃ | 2 | — | — | 2.0 | 75.0 |
| 12 | P(O p-Clφ)₃ | 2 | — | — | 0.5 | low |
| 13 | P(OCH₃)₃ | 1 | P(isopropyl)₃ | 1 | 48.0 | 95.0 |
| 14 | P(OCH₃)₃ | 1 | P(isopropyl)₃ | 2 | 91.0 | 98.1 |
| 15 | P(OCH₃)₃ | 2 | P(isopropyl)₃ | 2 | 77.0 | 98.3 |
| 16 | P(O Ethyl)₃ | 1 | P(isopropyl)₃ | 2 | 84.0 | 99.0 |
| 17 | P(O Ethyl)₃ | 2 | P(isopropyl)₃ | 2 | 88.0 | 96.5 |
| 18 | P(O isopropyl)₃ | 1 | P(isopropyl)₃ | 1 | 56.0 | 96.5 |
| 19 | P(O isopropyl)₃ | 1 | P(isopropyl)₃ | 2 | 85.0 | 99.0 |
| 20 | P(O isopropyl)₃ | 2 | P(isopropyl)₃ | 1 | 47.0 | 92.5 |
| 21 | P(O isopropyl)₃ | 2 | P(isopropyl)₃ | 2 | 98.0 | 98.5 |
| 22 | P(O n-butyl)₃ | 1 | P(isopropyl)₃ | 1 | 44.0 | 95.0 |
| 23 | P(O n-butyl)₃ | 1 | P(isopropyl)₃ | 2 | 82.0 | 98.5 |
| 24 | P(O n-butyl)₃ | 2 | P(isopropyl)₃ | 2 | 82.0 | 98.3 |
| 25 | P(O Phenyl)₃ | 1 | P(isopropyl)₃ | 1 | 11.0 | 98.0 |
| 26 | P(O Phenyl)₃ | 2 | P(isopropyl)₃ | 2 | 23.0 | 98.0 |
| 27 | P(O p-Clφ)₃ | 2 | P(isopropyl)₃ | 2 | 52.0 | 95.3 |
| 28 | P(O isopropyl)₃ | 1 | P(n-butyl)₃ | 1 | 17.0 | 79.0 |
| 29 | P(O isopropyl)₃ | 2 | P(n-butyl)₃ | 2 | 37.0 | 85.0 |
| 30 | P(O isopropyl)₃ | 1 | P(Phenyl)₃ | 1 | 9.4 | 85.0 |
| 31 | P(O isopropyl)₃ | 2 | P(Phenyl)₃ | 2 | 19.0 | 87.0 |
| 32 | P(O isopropyl)₃ | 1 | P(Ethyl)₃ | 1 | 14.0 | 77.0 |
| 33 | — | — | P(cyclohexyl)₃ | 1 | 25.0 | 97.0 |
| 34 | — | — | P(cyclohexyl)₃ | 2 | 40.0 | 98.0 |
| 35 | P(O ethyl)₃ | 1 | P(cyclohexyl)₃ | 2 | 62.0 | 97.0 |
| 36 | P(O isopropyl)₃ | 1 | P(cyclohexyl)₃ | 2 | 61.0 | 97.8 |
| 37 | P(O isopropyl)₃ | 2 | P(cyclohexyl)₃ | 2 | 65.0 | 96.0 |
| 38 | — | — | P(sec butyl)₃ | 2 | 25.0 | 97.5 |
| 39 | P(O isopropyl)₃ | 2 | P(sec butyl)₃ | 2 | 95.0 | 97.8 |
| 40 | — | — | P(t-butyl)₂ benzyl | 2 | 23.0 | 99.2 |
| 41 | P(O isopropyl)₃ | 2 | P(t-butyl)₂ benzyl | 2 | 82.0 | 98.2 |
|  | Phosphonite |  | Phosphine |  |  |  |
| 42 | P Phenyl (O n-butyl)₂ | 2 | — | — | 1.4 | 75.0 |
| 43 | P Phenyl (O n-butyl)₂ | 1 | P (isopropyl)₃ | 2 | 73.0 | 99.0 |
| 44 | P Phenyl (O n-butyl)₂ | 2 | P (Isopropyl)₃ | 2 | 80.0 | 98.6 |
| 45 | P t-butyl (OCH₃)₂ | 2 | — | — | 35.0 | 93.6 |
| 46 | P t-butyl (OCH₃)₂ | 2 | P (isopropyl)₃ | 2 | 95.0 | 98.0 |
| 47 | Pt-butyl (OCH₃)₂ | 4 | P (isopropyl)₃ | 2 | 80.0 | 98.6 |
| 48 | Pt-butyl (O benzyl)₂ | 2 | — | — | 26.0 | 94.0 |
| 49 | Pt-butyl (O benzyl)₂ | 2 | P(isopropyl)₃ | 2 | 72.0 | 98.3 |
| 50 | Pt-butyl (O benzyl)₂ | 1 | P(isopropyl)₃ | 1 | 59.0 | 97.8 |
| 51 | Pt-butyl (O isopropyl)₂ | 2 | — | — | 60.0 | 97.3 |

TABLE I-continued

| Example | | P/Pd Ratio | | P/Pd Ratio | Butadiene Conversion mol % | 1,7-Octadiene Selectivity mol % |
|---|---|---|---|---|---|---|
| 52 | P t-butyl (O isopropyl)₂ | 1 | — | — | 34.0 | 96.0 |
| 53 | P t-butyl (O isopropyl)₂ | 1 | P(isopropyl)₃ | 1 | 42.0 | 97.0 |
| 54 | P t-butyl (O isopropyl)₂ | 1 | P(isopropyl)₃ | 2 | 82.0 | 98.6 |
| | Phosphinite | | | | | |
| 55 | P(Phenyl)₂O n-butyl | 2 | — | — | 12.0 | 74.0 |
| 56 | P(Phenyl)₂O n-butyl | 2 | P(isopropyl)₃ | 2 | 86.0 | 98.5 |
| 57 | P(cyclohexyl)₂O CH₃ | 2 | — | — | 18.0 | 96.5 |
| 58 | P(cyclohexyl)₂O CH₃ | 2 | P(isopropyl)₃ | 2 | 60.0 | 98.0 |
| 59 | P(t-butyl)₂O benzyl | 1 | — | — | 31.0 | 98.6 |
| 60 | P(t-butyl)₂O benzyl | 2 | — | — | 39.0 | 98.8 |
| 61 | P(t-butyl)₂O benzyl | 4 | — | — | 51.0 | 99.3 |
| 62 | P(t-butyl)₂O benzyl | 1 | P(isopropyl)₃ | 1 | 47.0 | 98.9 |
| 63 | P(t-butyl)₂O benzyl | 2 | P(isopropyl)₃ | 2 | 61.0 | 99.3 |
| 64 | P(cyclohexyl)₂ O cyclohexyl | 1 | — | — | 55.0 | 95.3 |
| 65 | P(cyclohexyl)₂ O cyclohexyl | 2 | — | — | 80.0 | 98.0 |
| 66 | P(cyclohexyl)₂ O cyclohexyl | 1 | P(isopropyl)₃ | 1 | 97.0 | 98.1 |
| 67 | p(cyclohexyl)₂ O cyclohexyl | 2 | P(isopropyl)₃ | 2 | 98.5 | 99.0 |
| 68 | — | — | P(Phenyl)₃ | 2 | 8.4 | 87.0 |
| 69 | P(t-butyl)₂O benzyl | 1 | P(Phenyl)₃ | 1 | 30.0 | 91.3 |
| 70 | — | — | P(n-butyl)₃ | 2 | 21.0 | 89.0 |
| 71 | P(t-butyl)₂ O benzyl | 1 | P(n-butyl)₃ | 1 | 56.0 | 98.0 |
| | Phosphites | | Phosphinites | | | |
| 72 | — | — | P(t-butyl)₂O benzyl | 1 | 31.0 | 98.6 |
| 73 | — | — | P(t-butyl)₂O benzyl | 2 | 39.0 | 98.8 |
| 74 | — | — | P(t-butyl)₂O benzyl | 4 | 51.0 | 99.3 |
| 75 | P(OCH₃)₃ | 1 | — | — | 8.5 | 71.0 |
| 76 | P(OCH₃)₃ | 1 | P(t-butyl)₂O benzyl | 1 | 80.0 | 97.8 |
| 77 | P(O Ethyl)₃ | 1 | — | — | 5.2 | 67.0 |
| 78 | P(O Ethyl)₃ | 1 | P(t-butyl)₂O benzyl | 1 | 78.0 | 98.3 |
| 79 | P(O isopropyl)₃ | 1 | — | — | 5.5 | 59.0 |
| 80 | P(O isopropyl)₃ | 1 | P(t-butyl)₂O benzyl | 1 | 80.0 | 98.5 |
| 81 | P(O n-butyl)₃ | 1 | — | — | 15.5 | 56.0 |
| 82 | P(O n-butyl)₃ | 1 | P(t-butyl)₂O benzyl | 1 | 78.0 | 97.8 |
| 83 | P(O phenyl)₃ | 1 | — | — | 1.7 | 75.0 |
| 84 | P(O phenyl)₃ | 1 | P(t-butyl)₂O benzyl | 1 | 26.0 | 98.0 |
| 85 | — | — | P(cyclohexyl)₂O cyclohexyl | 1 | 55.0 | 95.3 |
| 86 | — | — | P(cyclohexyl)₂O cyclohexyl | 2 | 80.0 | 98.0 |
| 87 | P(o isopropyl)₃ | 1 | P(cyclohexyl)₂O cyclohexyl | 1 | 89.0 | 99.2 |
| 88 | P(n-butyl)₃ | 1 | P(cyclohexyl)₂O cyclohexyl | 1 | 43.0 | 95.0 |
| | Phosphites | | Phosphonites | | | |
| 89 | — | — | P t-butyl(O benzyl)₂ | 1 | 15.3 | 92.2 |
| 90 | — | — | P t-butyl(O benzyl)₂ | 2 | 26.0 | 94.0 |
| 91 | P(OCH₃)₃ | 1 | P t-butyl(O benzyl)₂ | 1 | 18.7 | 86.0 |
| 92 | P(O isopropyl)₃ | 1 | P t-butyl(O benzyl)₂ | 1 | 27.0 | 87.0 |
| 93 | — | — | P t-butyl(O propyl)₂ | 1 | 34.0 | 96.0 |
| 94 | P(O ethyl)₃ | 1 | P t-butyl(O propyl)₂ | 1 | 37.0 | 94.0 |
| 95 | P(O isopropyl)₃ | 1 | P t-butyl(O propyl)₂ | 1 | 42.0 | 97.0 |
| 96 | P(O phenyl)₃ | 2 | P t-butyl(O propyl)₂ | 1 | 20.0 | 96.4 |
| | Phosphonites | | Phosphinites | | | |
| 97 | P(t-butyl) (O benzyl)₂ | 1 | — | — | 15.3 | 92.2 |
| 98 | P(t-butyl) (O benzyl)₂ | 2 | — | — | 26.0 | 94.0 |
| 99 | — | — | P(t-butyl)₂O benzyl | 1 | 31.0 | 98.6 |
| 100 | — | — | P(t-butyl)₂O benzyl | 2 | 39.0 | 98.8 |
| 101 | P(t-butyl) (O | | | | | |

TABLE I-continued

| Example | | P/Pd Ratio | | P/Pd Ratio | Butadiene Conversion mol % | 1,7-Octadiene Selectivity mol % |
|---|---|---|---|---|---|---|
| 102 | benzyl)$_2$ | 1 | P(t-butyl)$_2$O benzyl P(cyclohexyl)$_2$O | 1 | 73.0 | 98.3 |
| 103 | — | — | cyclohexyl P(cyclohexyl)$_2$O | 1 | 55.0 | 95.3 |
|  | — | — | cyclohexyl P(cyclohexyl)$_2$O | 2 | 80.0 | 98.0 |
| 104 | P(t-butyl) (O benzyl) |  | cyclohexyl | 1 | 76.0 | 92.0 |

Illustrative Embodiment II

To an 80 milliliter glass-lined autoclave were charged $2.7 \times 10^{-5}$ moles of palladium acetylacetonate, 10 ml of dimethylsulfoxide, 2 g of butadiene, $1.85 \times 10^{-2}$ moles of formic acid and sufficient phosphorus ligand to provide the appropriate ligand to palladium ratio as shown in Table II below. The stirred reactor was heated to 40° C. for two hours, cooled and the product was analyzed by gas chromatography and mass spectrometry. The results are shown in Table II.

TABLE II

| Example | Phosphine | P/Pd Ratio | Phosphite | P/Pd Ratio | Butadiene Conversion Mol % | 1,7-Octadiene Selectivity Mol % |
|---|---|---|---|---|---|---|
| 105 | P(sec-butyl)$_3$ | 2 | — | — | 20.0 | 98.5 |
| 106 | P(sec-butyl)$_3$ | 2 | P(O-ethyl)$_3$ | 2 | 85.0 | 98.0 |

Illustrative Embodiment III

To an 80 milliliter glass-lined autoclave were charged $2.7 \times 10^{-5}$ moles of palladium acetylacetonate, 10 ml of dimethylsulfoxide, 2 g of butadiene, $1.85 \times 10^{-2}$ moles of sodium formate, 1 ml of H$_2$O and sufficient phosphorus ligand to provide the appropriate ligand to palladium ratio as shown in Table III below. The stirred reactor was heated to 40° C. for two hours, cooled and the product was analyzed by gas chromatography and mass spectrometry. The results are shown in Table III.

TABLE III

| Example | Phosphite | P/Pd Ratio | Phosphite | P/Pd Ratio | Butadiene Conversion Mol % | 1,7-Octadiene Selectivity Mol % |
|---|---|---|---|---|---|---|
| 107 | P(isopropyl)$_3$ | 2 | — | — | 27.0 | 97.0 |
| 108 | — | — | P(O-isopropyl)$_3$ | 2 | 13.0 | 93.0 |
| 109 | P(isopropyl)$_3$ | 2 | P(O-Isopropyl)$_3$ | 2 | 54.0 | 97.3 |

What is claimed is:

1. A process for preparing 1,7-octadiene which comprises hydrodimerizing butadiene in the presence of formic acid or a salt thereof, optionally a solvent, a catalytic amount of palladium and a mixture of tertiary organo phosphorus ligands comprising a first ligand having the formula (RO)$_a$PR$_b$ and a second ligand having the formula (RO)$_{a'}$PR$_{b'}$ wherein a+b equal 3, a is 0, 1 or 2, a'+b' equal 3, a' is 0, 1, 2 or 3, a is not the same as a', R is aryl, alkyl, aralkyl or alkaryl with less than about 20 carbon atoms wherein the Rs attached to the phosphorus and oxygen are the same or different and with at least one R of said first ligand being a sterically hindering moiety selected from benzyl or branched alkyl, aralkyl, alkenyl and cycloalkyl having from 3 to about 10 carbon atoms wih branching occuring at a carbon atom no more than two carbon atoms from the phosphorus atom.

2. The process of claim 1 wherein the temperature ranges from about 0° C. to about 100° C., the palladium ranges from about $10^{-1}$ to about $10^{-4}$ molar, the ratio of first ligand to palladium is at least 1 and the ratio of second ligand to palladium is at least 1.

3. A process for preparing 1,7-octadiene which comprises hydrodimerizing butadiene in the presence of formic acid or a salt thereof, optionally a solvent, a catalytic amount of palladium and a mixture of tertiary phosphorus ligands comprising a first ligand having the formula Z—P(RO)$_n$R$_p$ and a second ligand having the formula (RO)$_{a'}$PR$_{b'}$ wherein Z is a crosslinked synthetic resin, R is aryl, alkyl, aralkyl or alkaryl with less than about 20 carbon atoms wherein the Rs attached to phosphorus atom and oxygen atom are the same or different, n is 0, 1 or 2, p+n equals 2, a'+b' equals 3, a' is 0, 1, 2, or 3 and with at least one R of said first ligand being a sterically hindering moiety selected from benzyl, or branched alkyl, aralkyl, alkenyl and cycloalkyl having from 3 to about 10 carbon atoms with branching occuring at a carbon atom no more than two carbon atoms from the phosphorus atom.

4. The process of claim 3 wherein the temperature ranges from about 0° C. to about 100° C., the palladium ranges from about $10^{-1}$ to about $10^{-4}$ molar, the molar ratio of first ligand (basis phosphorus) to palladium is at least 1 and the molar ratio of second ligand (basis phosphorus) to palladium is at least 1.

5. A process for preparing 1,7-octadiene which comprises hydrodimerizing butadiene in the presence of formic acid or a salt thereof, optionally a solvent, a catalytic amount of palladium and a mixture of tertiary phosphorus ligands comprising a first ligand having the formula (RO)$_a$PR$_b$ and a second ligand having the formula Z—P(RO)$_n$R$_p$ wherein Z is a crosslinked synthetic resin, R is aryl, alkyl, aralkyl or alkaryl with less than about 20 carbon atoms wherein the Rs attached to the phosphorus and oxygen atoms are the same and different, a+b equals 3, a is 0, 1 or 2, n is 0, 1 or 2, p+n equals 2 and with at least one R of said first ligand being a sterically hindering moiety selected from benzyl, or branched alkyl, aralkyl, alkenyl and cycloalkyl having from 3 to about 10 carbon atoms with branching occurring at a carbon atom no more than two carbon atoms from the phosphorus atom.

6. The process of claim 5 wherein the temperature ranges from about 0° C. to about 100° C., the palladium ranges from about $10^{-1}$ to about $10^{-4}$ molar, the molar ratio of first ligand (basis phosphorus) to palladium is at least 1 and the molar ratio of second ligand (basis phosphorus) to palladium is at least 1.

7. The process of claim 3, 4, 5 or 6 where Z is selected from the group consisting of crosslinked polystyrene, poly(alpha-alkyl) acrylate, polycarbonate and polyamide.

8. The process of claims 1, 2, 3, 4, 5 or 6 wherein the sterically hindering moiety is selected from benzyl, isopropyl, cyclohexyl, isobutyl, sec-butyl and tert-butyl.

* * * * *